US006685813B2

(12) United States Patent
Williams et al.

(10) Patent No.: US 6,685,813 B2
(45) Date of Patent: Feb. 3, 2004

(54) TANDEM ISOTACHOPHORESIS/ZONE ELECTROPHORESIS METHOD AND SYSTEM

(75) Inventors: Stephen J. Williams, San Mateo, CA (US); Hong Dong Tan, San Jose, CA (US); Hung Pin Kao, Fremont, CA (US); Wyatt N. Vreeland, Chicago, IL (US)

(73) Assignee: Aclara Biosciences, Inc., Mountain View, CA (US)

( * ) Notice: Subject to any disclaimer, the term of this patent is extended or adjusted under 35 U.S.C. 154(b) by 0 days.

(21) Appl. No.: 09/933,993

(22) Filed: Aug. 20, 2001

(65) Prior Publication Data

US 2002/0079223 A1 Jun. 27, 2002

Related U.S. Application Data

(63) Continuation-in-part of application No. 09/780,638, filed on Feb. 10, 2001.
(60) Provisional application No. 60/185,035, filed on Feb. 25, 2000, and provisional application No. 60/182,049, filed on Feb. 11, 2000.

(51) Int. Cl.[7] .......................... B01D 59/02; B01D 59/42; B01D 59/50; B01D 61/42; B01D 61/58; C02F 1/469; C07K 1/26; C08F 2/58
(52) U.S. Cl. ...................................... 204/549
(58) Field of Search ......................... 204/549

(56) References Cited

U.S. PATENT DOCUMENTS

| | | | |
|---|---|---|---|
| 5,599,432 A | | 2/1997 | Manz et al. |
| 5,800,690 A | | 9/1998 | Chow et al. |
| 5,810,985 A | * | 9/1998 | Bao et al. ............. 204/451 |
| 5,858,187 A | * | 1/1999 | Ramsey et al. ....... 204/451 |
| 5,858,195 A | | 1/1999 | Ramsey |

(List continued on next page.)

FOREIGN PATENT DOCUMENTS

| | | |
|---|---|---|
| WO | WO 98/49548 | 11/1998 |
| WO | WO 98/54568 A1 | 12/1998 |
| WO | WO 99/10735 A1 | 3/1999 |

OTHER PUBLICATIONS

Jacobson and Ramsey, "Microchip electrophoresis with sample stacking," *Electrophoresis*, 16: 481–486 (1995).
Copy of PCT International Search Report from PCT/US02/26393.

(List continued on next page.)

*Primary Examiner*—Mark L. Bell
*Assistant Examiner*—Jennine Brown
(74) *Attorney, Agent, or Firm*—Linda R. Judge; LeeAnn Gorthey; Perkins Coie LLP

(57) ABSTRACT

A method of separating components having a given negative or positive charge and contained in a sample is disclosed. The method involves, in one embodiment, loading a microchannel with a sample, placed between a trailing-edge electrolyte having a selected concentration of a titratable species, and a leading-edge electrolyte. With the application of a voltage potential across the microchannel, charged components in the sample stack by isotachophoresis, and electrolytic hydroxyl or hydrogen ions formed by electrolysis at the upstream-end electrode migrate into the trailing-edge ion buffer, titrating the titratable species therein, where the concentration of the titratable species in the trailing-edge electrolyte is selected, in relation to the lengths of the upstream channel region and sample-loading volume, to permit the sample to stack into a relatively small sample volume before electrolytic-ion migration from the upstream electrode into and through the sample-volume region is effective to overtake the charged sample components. With continued application of an electric potential across the channel ends, charged sample components in the stacked sample volume separate by zone electrophoresis.

14 Claims, 11 Drawing Sheets

TRIS leading     low electric field

U.S. PATENT DOCUMENTS

| | | | |
|---|---|---|---|
| 5,869,004 | A | 2/1999 | Parce et al. |
| 5,965,001 | A | 10/1999 | Chow et al. |
| 6,174,675 | B1 * | 1/2001 | Chow et al. ................. 204/164 |
| 6,251,691 | B1 * | 6/2001 | Seul .......................... 204/400 |
| 6,368,871 | B1 * | 4/2002 | Christel et al. ............. 204/450 |
| 6,387,707 | B1 * | 5/2002 | Seul et al. ..................... 422/50 |
| 6,432,290 | B1 * | 8/2002 | Harrison et al. ............ 204/451 |
| 6,475,441 | B1 | 11/2002 | Parce et al. |

OTHER PUBLICATIONS

Foret, Frantisek et al., "On–column transient and coupled column isotachophoretic preconcentration of protein samples in capillary zone electrophoresis", *Journal of Chromatography*, 608:3–12, 1992.

Reinhoud, N.J. et al., "Capillary isotachophoretic analyte focusing for capillary electrophoresis with mass spectrometric detection using electrospray ionization", *Journal of Chromatography*, 627:263–271, 1992.

Krivankova, Ludmila et al., "Synergism of capillary isotachophoresis and capillary zone electrophoresis", *Journal of Chromatography B*, 689:13–34, 1997.

Waterval, Joop C.M. et al., "Development and validation of transient isotachophoretic capillary zone electrophoresis for determination of peptides", *Electrophoresis* 19:3171–3177, 1998.

Dankova, Mariana et al., "Capillary zone electrophoresis separations of enantiomers present in complex ionic matrices with on–line isotachophoretic sample pretreatment", *Journal of Chromatography A*, 838:31–43, Apr. 9, 1999.

Masar, Marian et al., "Determination of organic acids and inorganic anions in wine by isotachophoresis on a planar chip", *Journal of Chromatography A*, 916:167–174, 2001.

Chen, Shujun et al., "Automated Instrumentation for Comprehensive Isotachophoresis—Capillary Zone Electrophoresis", *Anal. Chem.* 72:816–820, 2000.

Pier Giorgio Righetti (ED): "Capillary Electrophoresis in Analytical Biotechnology", CRC Press, New York XP008002033, pp. 84–87, 1996.

Jacobson, Stephen C. et al., "Effects of Injection Schemes and Column Geometry on the Performance of Microchip Electrophoresis Devices", *Anal. Chem.* 66, pp. 1107–1113, 1994.

Quirino, Joselito P. et al., "Sample stacking of cationic and anionic analytes in capillary electrophoresis", *Journal of Chromatography A*, 902, pp. 119–135, 2000.

Gebauer, Petr et al., "Sample self–stacking in zone electrophoresis. Theoretical description of the zone electrophoretic separation of minor compounds in the presence of bulk amounts of a sample component with high mobility and like charge", *Journal of Chromatography, 608*, pp. 47–57, 1992.

Guzman, Norberto A. et al., "New Directions for Concentration Sensitivity Enhancement in CE and Microchip–Technology", *LCGC*, vol. 19, No. 1, Jan. 2001.

Yang, Hua et al., "Sample stacking in laboratory–on–a–chip devices", *Journal of Chromatography A*, 924, pp. 155–163, 2001.

* cited by examiner

TANDEM ISOTACHOPHORESIS/ZONE ELECTROPHORESIS METHOD AND SYSTEM

This application is a continuation-in-part of U.S. patent application for Microfluidic Device with Sample Injector, Ser. No. 09/780,638, filed Feb. 10, 2001, which in turn claims priority to U.S. provisional patent applications Serial No. 60/182,049 filed Feb. 11, 2000 and Serial No. 60/185,035, filed Feb. 25, 2000, all of which are incorporated herein by reference.

FIELD OF THE INVENTION

The field of this invention is related to sample loading, stacking, and separation in a microfluidics device.

BACKGROUND

Microfluidics is revolutionizing the way activities are performed in a substantial proportion of chemical and physical operations. One area of microfluidics is the manipulation of small volumes of liquids or liquid compositions on a solid substrate, where a network of channels and reservoirs are present. By employing electric fields with electrically conducting liquids, volumes and/or ions can be moved from one site to another, different solutions formed by mixing liquids and/or ions, reactions performed, separations performed, and analyses carried out. In fact, in common parlance, the system has been referred to as "a laboratory on a chip." Various prior art devices of this type include U.S. Pat. Nos. 6,010,608, 6,010,607, 6,001,229, 5,858,195, and 5,858,187 which are a family of applications concerned with injection of sample solutions. See also, U.S. Pat. No. 5,599,432, EPA 0620432, and Verheggen et al., J. of Chromatography 452 (1988) 615–622.

In many of the operations, there is an interest in electrophoretically separating multiple sample components contained in dilute samples, e.g., samples with concentrations of sample components in the femtomolar to nanomolar range. Efficient electrophoretic injection of dilute samples frequently results in large sample volumes and poor resolution of the sample components.

It would thus be desirable to provide an electrophoretic system for improved separation and resolution of sample components, particularly where the sample components are present at nanomolar concentrations or less. It would be further desirable to provide a method of adjusting separation conditions as to maximize electrophoretic separation and resolution.

SUMMARY OF THE INVENTION

In one aspect, the invention includes a microfluidics system for use in electrophoretic separation of components having a given negative or positive charge and contained in a dilute sample. The system includes a microfluidics device having a substrate and a channel network formed therein. The channel network has a separation channel and first and second side channels that intersect the separation channel at axially spaced positions therealong. The two side channels partition the separation microchannel, in an upstream to downstream direction, into an upstream channel region upstream of intersection with the first side channel, a sample-volume channel region between the intersections of the two side channels, and a downstream separation channel region downstream of the second side channel intersection. The ratio of the lengths of the sample-volume region to the separation channel is between about 1:50 to 1:1.

The channel network is designed to be loaded initially by filling the upstream channel region with a trailing-edge electrolyte, filling the sample-volume channel region with the dilute sample, and filling the separation channel region, with a leading-edge (LE) electrolyte.

Also included in the device are upstream and downstream reservoirs communicating with the upstream and downstream ends of the separation channel, respectively, and first and second reservoirs communicating with the first and second side channels, respectively, opposite the side channel intersections with the separation channel. Upstream and downstream electrodes in the system are adapted to contact liquid contained in the upstream and downstream reservoirs, respectively.

A control unit in the system includes a power source for applying a voltage potential across the upstream and downstream electrodes, under conditions such that, with the upstream channel region filled with a trailing-edge electrolyte, the sample-volume channel region filled with the dilute sample, and the separation channel region filled with a leading-edge electrolyte, the sample stacks into a relatively small sample volume before hydroxyl- or hydrogen-ion migration into and through the sample-volume region is effective to overtake the charged sample components, wherein continued application of an electric potential across the channel ends causes charged sample components in the stacked sample volume to separate by zone electrophoresis.

In one general embodiment, the upstream channel region is filled with a trailing-edge electrolyte containing a selected concentration of a titratable species. Application of the voltage potential is effective to cause charged components in the sample to stack by isotachophoresis, and, at the same time, electrolytic hydroxyl or hydrogen ions formed by electrolysis at the upstream-end electrode to migrate into the trailing-edge electrolyte, titrating the titratable species therein. The concentration of titratable species in the trailing-edge electrolyte is selected, in relation to the lengths of the upstream channel region and sample-loading volume, to permit the sample to stack into a relatively small sample volume before electrolytic-ion migration from the upstream electrode into and through the sample-volume region is effective to overtake the charged sample components, wherein continued application of an electric potential across the channel ends causes charged sample components in the stacked sample volume to separate by zone electrophoresis.

In another general embodiment, the upstream channel region includes a pair of upstream reservoirs, one containing the TE electrolyte, and the other containing a source of hydroxyl or hydrogen ions, e.g., a basic or acidic solution. The control unit is operated to initially apply a voltage potential across electrodes in contact with the one upstream reservoir and the downstream channel end, and subsequently, to apply a voltage potential across electrodes in contact with the other upstream reservoir and the downstream channel end.

The system may be used to detect charged sample components present at nanomolar concentrations or less, where the ratio of the lengths of the sample-volume region to the separation channel in the device is between about 1:50 to 1:1.

The system may include one of a plurality of different microfluidics devices having different channel-length ratios between 1:50 and 1:1. In this embodiment, the control unit is operable to calculate the approximate concentration of titratable species in the trailing-ion electrolyte required for any selected microfluidics device length ratio.

The control unit may also be operable to load (i) the downstream channel region with the leading-edge electrolyte, by applying an electrokinetic voltage across the downstream reservoir and one of the first and second reservoirs, (ii) the upstream channel region with the trailing-edge electrolyte, by applying an electrokinetic voltage across the upstream reservoir and one of the first and second reservoirs, and (iii) the sample volume region by applying a fluid-motive force effective to move sample contained in one of the first and second reservoirs through the sample-volume region and toward the other of the first and second reservoirs. The device in this embodiment may include first and second electrodes adapted to contact liquid contained in the first and second reservoirs, respectively, where the control unit is operable to load the sample volume region by applying an electrokinetic voltage across the first and second electrodes.

The control unit is preferably operable to apply having across the upstream and downstream electrodes, a voltage potential characterized by a constant current, a constant voltage or constant power.

In another aspect, the invention includes a method of separating components having a given negative or positive charge and contained in a dilute sample. Initially a separation microchannel having, in an upstream to downstream direction, an upstream channel region, a sample-volume channel region, and a downstream separation channel region, is loaded so as to fill the upstream channel region with a trailing-edge electrolyte containing a selected concentration of a titratable species, the sample-volume channel region, with the dilute sample, and the separation channel region, with a leading-edge electrolyte.

There is then created an electrical field potential across the channel, by applying a voltage potential across electrodes in contact with the upstream and downstream channel ends, initially causing charged components in the sample to stack by isotachophoresis, and subsequently causing hydroxyl or hydrogen ions to migrate into the trailing-edge electrolyte, titrating the titratable species therein, under conditions that that permit the sample to stack into a relatively small sample volume before hydroxyl- or hydrogen-ion migration into and through the sample-volume region is effective to overtake the charged sample components, wherein continued application of an electric potential across the channel ends causes charged sample components in the stacked sample volume to separate by zone electrophoresis.

In one general embodiment, the upstream channel region is filled with a trailing-edge electrolyte containing a selected concentration of a titratable species. Application of the voltage potential is effective to cause charged components in said sample to stack by isotachophoresis, and, at the same time, electrolytic hydroxyl or hydrogen ions formed by electrolysis at the upstream-end electrode to migrate into the trailing-edge electrolyte, titrating the titratable species therein. The concentration of titratable species in the trailing-edge electrolyte is selected, in relation to the lengths of the upstream channel region and sample-loading volume, to permit the sample to stack into a relatively small sample volume before electrolytic-ion migration from the upstream electrode into and through the sample-volume region is effective to overtake the charged sample components, wherein continued application of an electric potential across the channel ends causes charged sample components in the stacked sample volume to separate by zone electrophoresis.

The trailing-edge electrolyte preferably includes a trailing-edge ion and a titratable counter-ion buffer at said selected concentration. Where the electrolytic ions formed at the upstream-end electrode are hydroxyl ions, the titratable counter-ion buffer may be a TRIS buffer.

In another general embodiment, the upstream channel region includes a pair of upstream reservoirs, one containing the trailing-edge electrolyte, and the other containing a source of hydroxyl or hydrogen ions. Initially a voltage potential is applied across electrodes in contact with the one upstream reservoir and the downstream channel end, and subsequently, a voltage potential is applied across electrodes in contact with the other upstream reservoir and the downstream channel end.

For use in detecting charged sample components present at nanomolar concentrations or less, the ratio of sample volume before and after isotachophoretic stacking is at least about 10:1, and may be at least about 50:1. For in detecting charged sample components present at picomolar or less concentrations, the ratio of sample volume before and after isotachophoretic stacking may be at least about 100:1.

The ratio of the lengths of the sample-volume region to the separation channel is preferably between about 1:50 to 1:1, more preferably between about 1:10 to 1:2.

In one exemplary method, the leading-edge electrolyte contains a negatively charged leading-edge ion having an effective conductivity greater than that of the sample ions and a concentration between 1–50 mM, the trailing-edge electrolyte contains a negatively charged trailing-edge ion having an effective conductivity lower than that of the sample ions and a concentration of between 1–50 mM, and both electrolytes have a positively charged buffer at a selected concentration between about 2 and 50 mM.

For use in separating a plurality of electrophoretic tags contained in a sample, each tag may have a detectable moiety and a mobility modifier that confers on the tag, a unique electrophoretic mobility. The method further includes the steps, after separating the tags electrophoretically, of detecting the separated tags, and from their electrophoretic mobilities and concentration, obtaining information about a biomolecular interaction.

Where the tags are contained on branched polymer structures and linked thereto through photo-labile linkages, the method may further include the step, after permitting branched structures in the sample to stack into a relatively small sample volume, of irradiating the branched structures to release the tags therefrom. Continued application of an electric potential across the channel ends causes the tags in the stacked sample volume to separate by zone electrophoresis.

These and other objects of the invention will become more fully apparent when the following detailed description of the invention is read in conjunction with the accompanying drawings.

DETAILED DESCRIPTION OF THE INVENTION

I. Microfluidic system

Figure 1A:
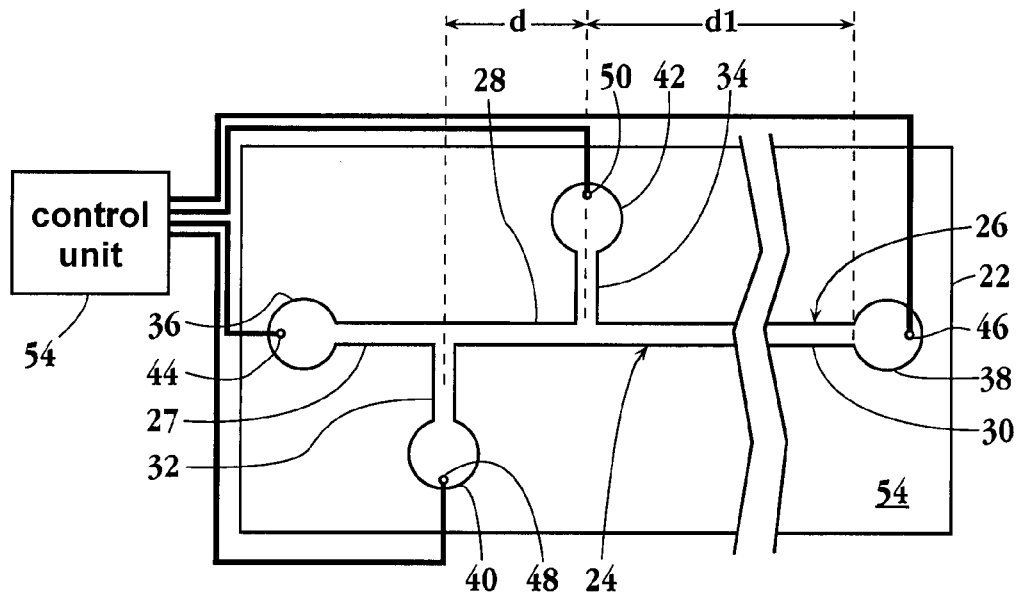
FIG. 1A illustrates a microfluidics system constructed in accordance with the present invention, for carrying out the separation method of the invention.

The invention includes, in one aspect, a microfluidic system for use in electrophoretic separation of components having a given negative or positive charge and contained in a dilute sample. By "sample" is meant an aqueous sample containing one or more charged components which can be separated electrophoretically, and preferably detected by standard optical techniques applicable to capillary zone electrophoresis. By "dilute sample" is meant a sample in which at least one of the components to be separated and detected is present at a concentration as low as 100 fM (femptomolar), typically 1 pM (picomolar) to higher concentrations, e.g., several hundred nanomolar of higher, preferably in the 1–500 pM range.

One exemplary system in accordance with the invention is shown at 22 in FIG. 1. The system includes a microfluidics device 24 having formed therein one or more channel networks, such as network 26 composed of a separation microchannel 26 having, in an upstream to downstream direction, an upstream channel region 27, a sample-volume channel region 28, and a downstream separation channel region 30. The sample-loading region is defined, at its upstream end, by a first side channel 32 and a second side channel 34 which intersects the separation channel at axial spaced positions, as indicated. More specifically, the length of the sample-loading region d is measured as the distance between the upstream side of the first channel, or a first-channel region close to the upstream side, and the downstream side of the second channel, or a region adjacent the downstream channel side, as shown. The downstream separation region has a length d'. In preferred embodiments of the invention, the ratio of the lengths of the sample-volume region to the separation channel in the device, d:d', is between about 1:50 to 1:1.

As will be discussed below, the system may include a plurality of devices of the types illustrated, each with a different selected d:d' ratio, e.g., devices having selected ratios of 1:50, 1:20, 1:10, 1:5, 1:2, and 1:1, where the particular device selected has an optimal ratio for the component separation desired. Although only a single channel network is shown, the device may include an array of channel networks, each having the general features described for network 26. In this embodiment, the device may include micropatterned conductors connecting each of the corresponding reservoirs in the networks to a common lead for connection to the control unit.

The separation channel terminates and is in fluid communication at its upstream and downstream ends with upstream and downstream reservoirs 36, 38, respectively. Similarly, the first and second side channels terminate and are in fluid communication with first and second reservoirs 40, 42. Each reservoir contains or is adapted to receive an electrode, which may be formed on the substrate or formed independently, e.g., on an electrode plate for placement on the substrate for electrode contact with liquid in the associated reservoirs. The electrodes associated with reservoirs 36, 38, 40, 42 are indicated at 44, 46, 48, 50, respectively. Each electrode is operatively connected to a control unit or voltage controller 54, which operates in various modes described below.

Figure 1B:
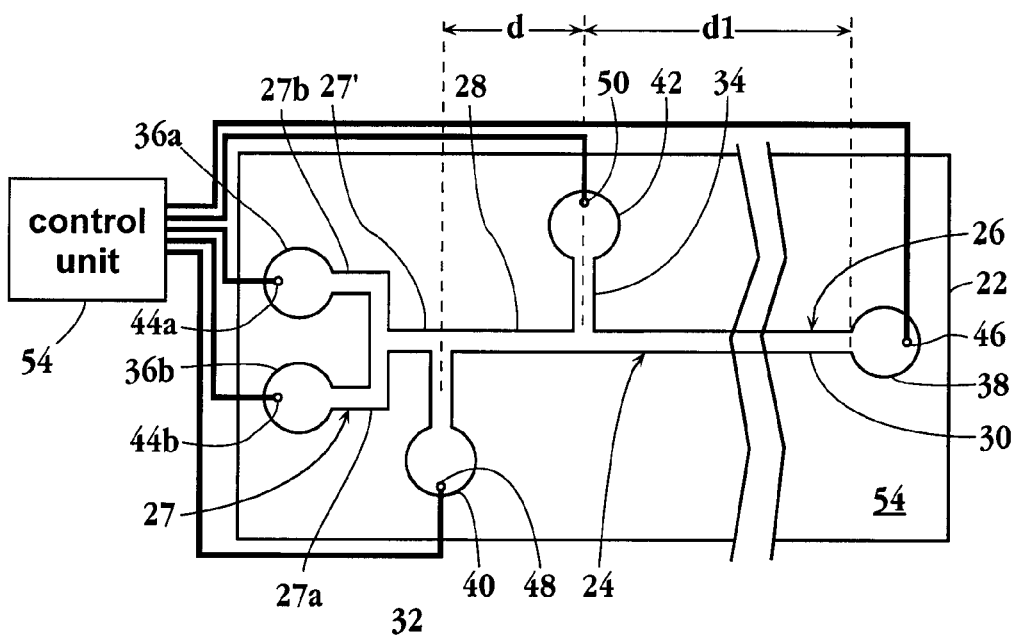
FIG. 1B illustrates another embodiment of a microfluidics device constructed in accordance with the invention.

FIG. 1B shows a modified system 24' having substantially the same components as mentioned above, and indicated by the same reference numerals, except as follows. Upstream channel region 27' is a Y-shaped channel having one arm 27a that terminates at one upstream reservoir 36a, and a second arm 27b that terminates in another upstream reservoir 36a. The control unit is operatively connected to electrodes 44b, and 44a in the two reservoirs, through the conductor connections shown.

As will be seen below, the electrodes in first and second reservoirs 40, 42, respectively, are used for moving fluid material in and out of the reservoirs electrokinetically, e.g., by electroosmotic flow (EOF). Alternatively, fluid movement in and out of the electrodes may be effected by a pressure or vacuum source operatively connected to the first and second reservoirs, and under the control of the control unit.

Considering the fabrication of the microfluidics device in the system, the channel network may be conventionally formed on a substrate or card 52, and covered by a transparent cover or film 54 which is attached or bonded to the card conventionally. The substrate in which the channels are present will generally have a thickness of at least about 20 $\mu$m, more usually at least about 40 $\mu$m, and not more than about 0.5 cm, usually not more than about 0.25 cm. The width of the substrate will be determined by the number of units to be accommodated and may be as small as about 2 mm and up to about 6 cm or more. The dimension in the other direction will generally be at least about 0.5 cm and not more than about 50 cm, usually not more than about 20 cm.

The substrate may be a flexible film or relatively inflexible solid, where the microstructures, such as reservoirs and channels, may be provided by embossing, molding, machining, etc. The channel dimensions will generally be in the range of about 0.1 $\mu$m to 1 mm deep and about 0.5 $\mu$m to 1 mm wide, where the cross-section will generally be 0.1 $\mu$m$^2$ to about 1 mm$^2$. The channel lengths will vary widely depending on the operation for which the channel is to be used, generally being in the range of about 0.05 mm to 50 cm, more usually in the range of about 0.5 mm to 20 cm. The main and side channels may have the same or different cross-sectional areas, as well as the same or different shapes. As noted above, the ratios of the lengths of the sample-loading region and the separation region is typically a selected ratio of 1:50 to 1:1.

The reservoirs will generally have volumes in the range of about 10 nl to 100 $\mu$l; more usually have volumes in the range of about 500 nl to 10 $\mu$l. The reservoirs may be cylindrically shaped, conically shaped, e.g. the frustum, or other regular shape.

The fabrication of the device may include the substrate comprising the microfeatures, a supporting film, an enclosing film, or combinations thereof. A supporting film will generally be at least about 40 $\mu$m and not more than about 5 mm thick. The film used to enclose the channels and the bottom of the reservoirs will generally have a thickness in the range of about 10 $\mu$m to 2 mm, more usually in the range of about 20 $\mu$m to 1 mm. The selected thickness may be controlled by the desire for good heat transfer, e.g. temperature control, but otherwise will usually be one of convenience and assurance of good sealing and the manner in which the devices will be used to accommodate instrumentation. The enclosing film, where the bottom of the substrate is totally closed, will also have a thickness coming within the above range, and will include perforations in register with the reservoirs or other feature requiring access, while enclosing the channels. Therefore, the ranges are not critical.

As indicated, the substrate may be a flexible film or inflexible solid, so the method of fabrication will vary with the nature of the substrate. For embossing, at least two films will be used, where the films may be drawn from rolls, one film embossed and the other film adhered to the embossed film to provide a physical support. The individual units may be scored, so as to be capable of being used separately, or the roll of devices retained intact. See, for example, application serial no. PCT/98/21869. Where the devices are fabricated individually, they will usually be molded, using conventional molding techniques. The substrates and accompanying film will generally be plastic, particularly organic polymers, where the polymers include addition polymers, such as acrylates, methacrylates, polyolefins, polystyrene, etc. or condensation polymers, such as polyethers, polyesters, polyamides, polyimides, dialkyl siloxanes, or norborane (Zeonor-type) polymers, although glasses, silicon or other material may be employed. Desirably, the polymers will have low fluorescence inherently or can be made so by additives or bleaching, e.g. photobleaching. A film will usually be placed over the substrate to at least enclose the channels, which film will usually have openings for communicating with the reservoirs and, where appropriate, introducing electrodes into the reservoirs. The enclosing film will be adhered to a substrate by any convenient means, such as thermal bonding, adhesives, etc. The literature has many examples of adhering such films, see, for example, U.S. Pat. Nos. 4,558,333; and 5,500,071.

The control unit includes a power source or voltage sources which is operatively connected to the electrodes in the device, as shown. The power source is under the control of an electronic controller in the control device. The controller determines the sequence and timing of voltages applied to the electrodes, and the voltage levels, in carrying out the method of the invention. The operation and design of the controller will be appreciated from the operation of the device described below.

II. Sample-component separation method

The system described above is designed to carry out a separation method in accordance with the invention. The separation method involves an initial sample-staking step carried out under isotachophoretic (ITP) conditions, as will be described in Section A. In accordance with an important feature of the invention, the electrolyte components used in the device are selected, particularly in relation to the length of the sample volume region, i.e., total sample volume, to permit the sample to stack into a small volume by ITP, before electrolyte conditions, or electrode control, shifts in a way that leads to sample separation by capillary electrophoresis (CE).

A. Isotachophoretic separation

The theory of ITP separation has been described, e.g., in "Capillary Electrophoresis in Analytical Biotechnology", Righetti, P. G., ed, 1996, CRC Press, pp. 84–87. Briefly, with reference to FIGS. 2A and 2B, a sample 58 containing components with different electrophoretic mobilities is placed between an electrolyte 60 with a leading edge ion and an electrolyte 62 containing a terminating or trailing-edge ion. In the present invention, the components are placed in a capillary tube, a section of which is shown at 56. The leading edge ion is a small ion, such as the chloride ion, having an electrophoretic mobility greater than that of any of the sample components. The counter-ion of the leading-edge ion is preferably chosen for its ability to buffer the solution.

Similarly, the trailing edge ion is one having an electrophoretic mobility lower than the slowest-migrating sample components. According to an important feature of the present invention, at least one of the trailing ion or counter-ion is a titratable ionic species, that is, a compound which has a titratable acid or base group. With the application of a voltage potential across the sample, sample components will band, by migration through the sample, until the fastest moving sample components are concentrated adjacent the leading-edge electrolyte and the slowest moving components, against the trailing edge electrolyte.

In the figures, the sample components to be separated are negatively charged, as are the leading- and trailing-ions, and the polarity of voltage is applied with the polarity shown, to attract the negatively charged components toward the right in the figures. Because the electric field across each section of the system is inversely proportional to the conductivity in that section, the section associated with the leading-edge ion is characterized by a relatively low electric field, and the section associated with the trailing-edge ion, with a relatively high electric field.

It is this different electric field or voltage gradient that maintains the sample components in a narrow band of sample components, each separated on the basis of their electrophoretic mobilities, once the sample components have staked into a narrow band. Sample ions that diffuse back into the trailing electrolyte "speed up" under the higher electric field. Similarly, sample ions that diffuse forward into the leading electrolyte slow down under the lower electric field. At the same time, each sample component migrates to a position closely adjacent the sample components nearest in electrophoretic mobility, causing the components to stack into a tight sample band of separated components between the leading- and trailing-ion electrolytes.

Figure 3A:
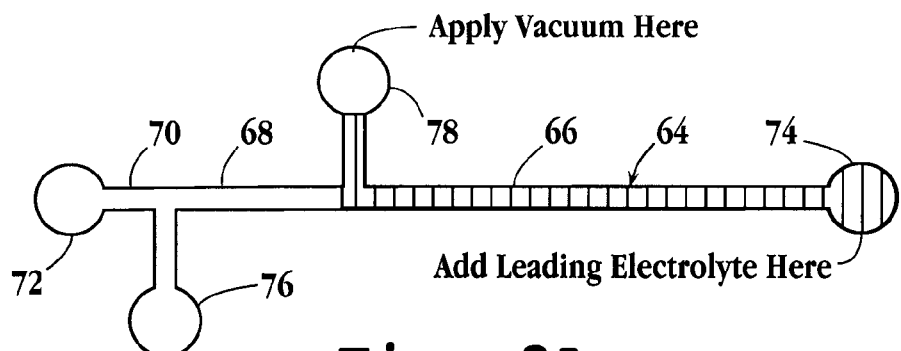
FIGS. 3A–3D illustrate successive steps in loading a microfluidics device in the method of the invention.
Figure 3B:
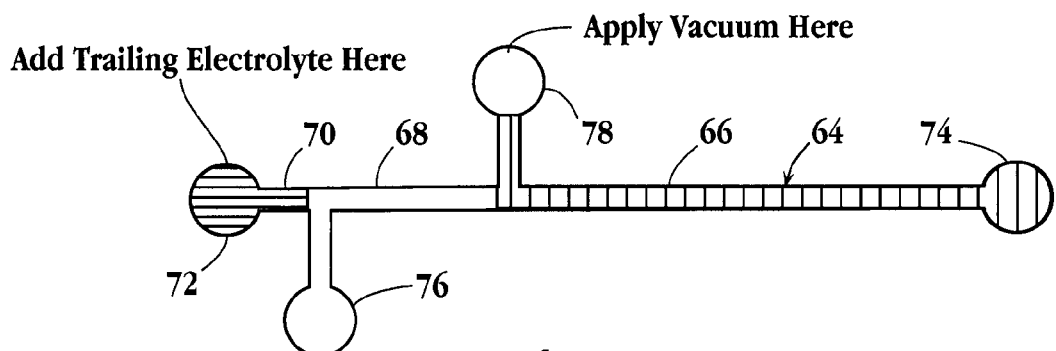
Figure 3C:
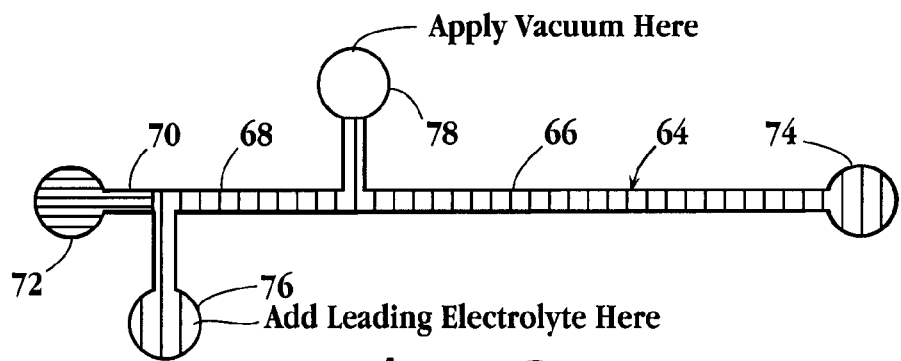
Figure 3D:
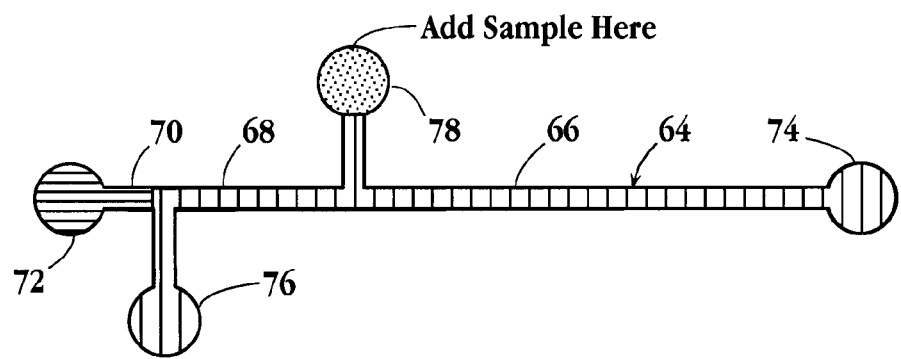

FIGS. 3A–3B show steps in the loading a sample in a microfluidics device of the type described above, for initial ITP stacking. The figures shows a channel network 64 having a separation channel intersected by two side channels, dividing the separation channel into three segments 66, 68, 70, as described above. The channel network includes the four reservoirs 72, 74, 76, 78 communicating with the channel segments shown. The network is loaded for ITP separation by adding the leading electrolyte to reservoir 74 and drawing the electrolyte toward reservoir 78, either by applying a vacuum to reservoir 78 or by applying a voltage potential across the two reservoirs, to move the electrolyte, as seen in FIG. 3A. Trailing electrolyte is added to reservoir 72, and this material is then drawn toward reservoir 78, as above, and as illustrated in FIG. 3B. The sample-volume segment 68 is then filled with leading electrolyte by drawing the electrolyte from reservoir 76 toward reservoir 78, as in FIG. 3C. Finally, sample containing trailing electrolyte is placed in reservoir 78, as shown in FIG. 3D. When a voltage potential is placed across reservoirs 76, 78, sample material fills the sample-volume region between the two reservoirs, in effect, drawing the sample into the LE electrolyte contained in the sample-volume region.

Figure 2A:
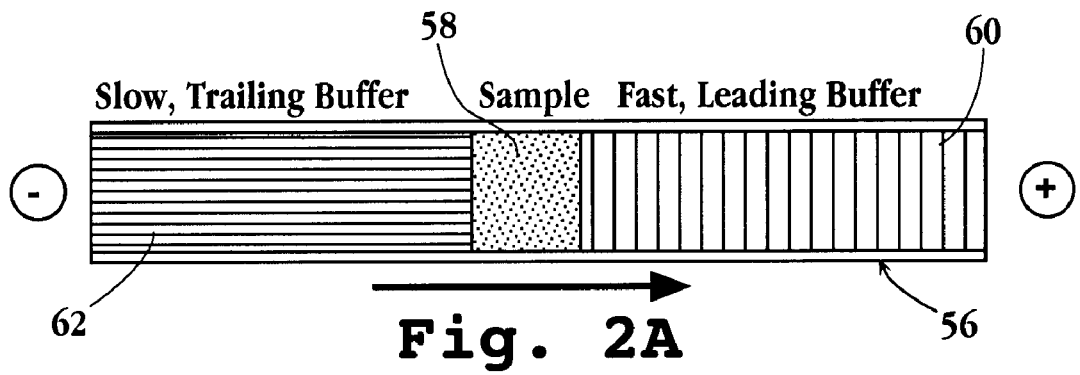
FIGS. 2A and 2B illustrate the general principle of isotachophoresis (ITP) separation of charged components in a sample in terms of buffer components (2A) and electric filed strength (2B)
Figure 2B:
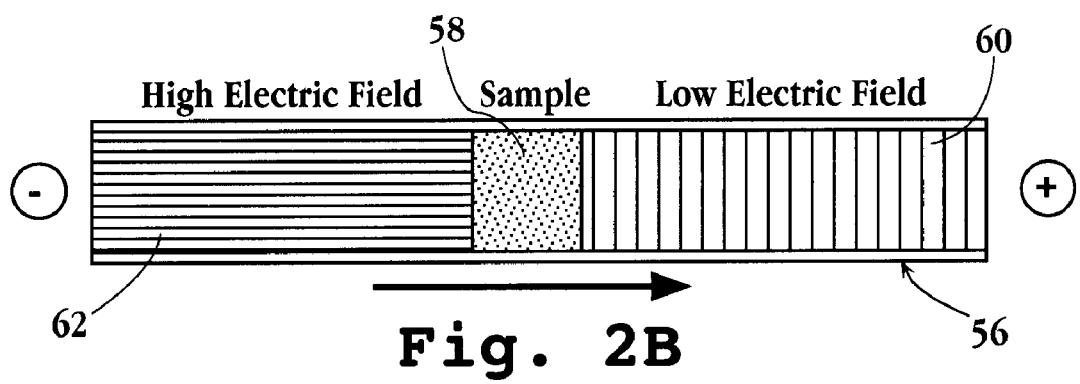

ITP stacking is achieved by applying a voltage potential across reservoirs 72, 74, with the polarity illustrated in FIGS. 2A and 2B, causing stacking of sample components in the sample-loading region or segment between the leading and trailing electrolytes.

Figure 4A:
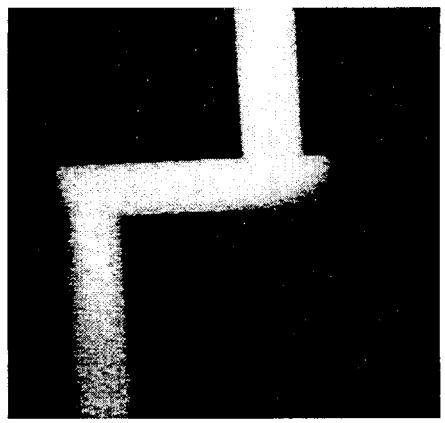
FIGS. 4A–4D illustrate CCD images of a fluorescent sample stacking in two different-length sample-volume regions.
Figure 4B:
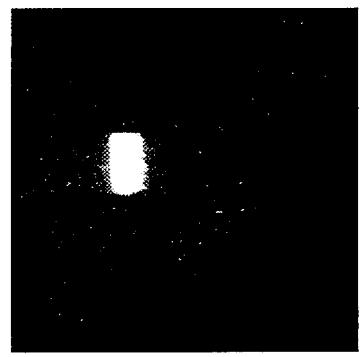
Figure 4C:
Figure 4D:
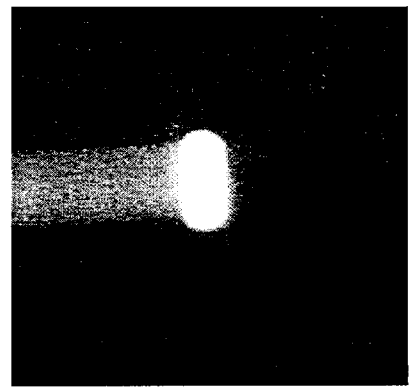

The ability of the ITP system to stack the sample components in large sample volumes is shown in FIGS. 4A–4D. In FIG. 4A, the sample loading region between the two side channels is 250 microns in length, and contains a total sample volume of about 500 $\mu$L. As shown in FIG. 4B, ITP stacking is effective to stack the sample band into a band of length of about 29 microns, i.e., about an 8.6 fold concentration of the sample components. This effective is even more dramatic with longer sample-loading regions, as illustrated in FIGS. 4C and 4D. Here a sample in a sample-loading region 3 mm in length is concentrated by ITP to a sample band having a length of about 31 microns, i.e., nearly a 100 fold concentration factor. In the ITP stacking phase of the invention, the ratio of sample volume before and after ITP stacking is preferably at least about 10:1, and may be as great as 50:1 or higher, e.g., 100:1 or more.

Figure 5A:
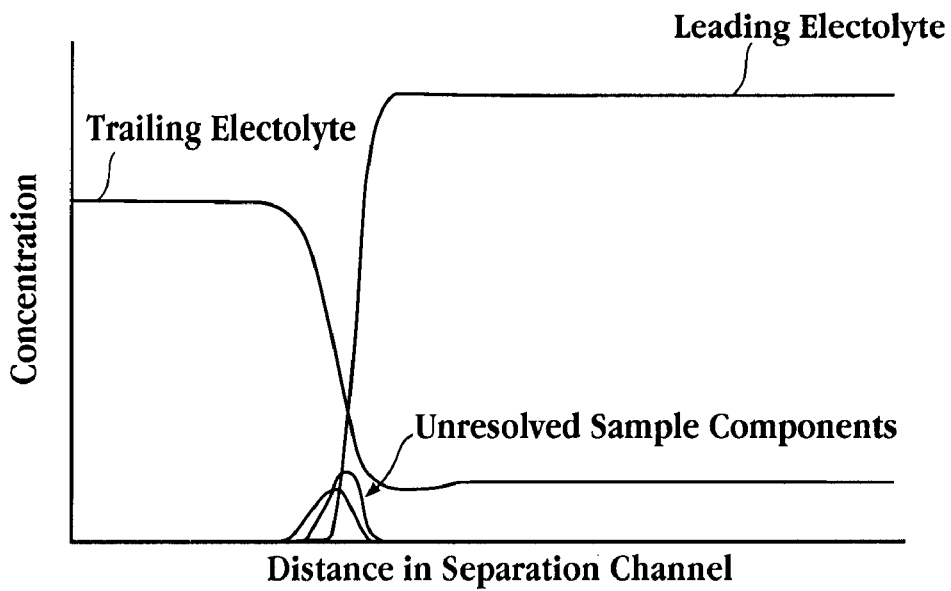
FIGS. 5A and 5B illustrate limitations of ITP separation with ultradilute samples, showing in FIG. 5A, a plot of sample component concentration as a function distance in separation channel, and in FIG. 5B, the inability to achieve resolution of different components.
Figure 5B:
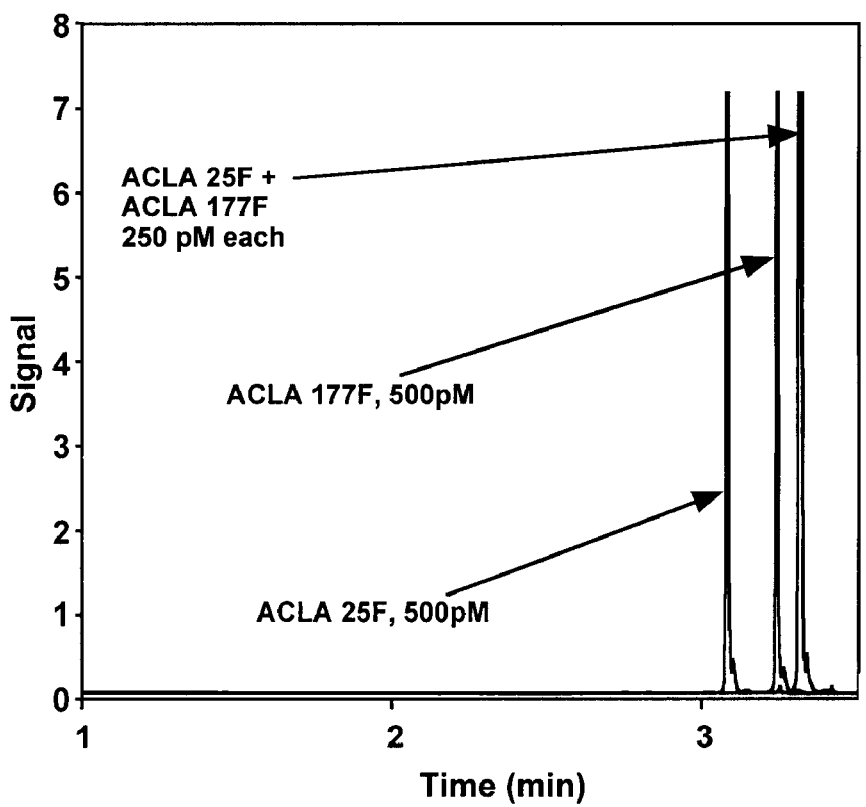

It can be appreciated from the foregoing that initial ITP stacking provides excellent stacking efficiency, especially for samples placed in relatively large sample-loading volumes. In particular, this allows for efficient concentration of very dilute samples by a factor of 100 or more, depending on the length of the sample-loading regions. The limitation of ITP, however, is relatively poor resolution of dilute sample components. For extremely dilute sample components, the band width required to obtain a function-specified concentration is less than the electrical discontinuity boundary thickness. As a result, dilute sample components tend to concentrate into a single narrow band with undetectable resolution. This is illustrated in FIG. 5A, which shows unresolved samples components at the interface between the leading and trailing electrolyte. FIG. 5B shows ITP profiles for dilute samples injected in an initial injection plug of 3 mm, and containing sample a fluorescent molecule at 500 pM concentration and a second fluorescent molecule, with a different electrophoretic mobility, also at a 500 pM concentration. As seen, the ITP system is unable to resolve the two species at the low concentration of sample components.

B. Combined ITP and capillary zone electrophoresis

As noted above, ITP produces high efficiency separation, but poor spatial separation of analytes for very dilute sample components. CZE, on the other hand, is less efficient but is better able to spatially resolve dilute sample components of different electrophoretic mobility. As will be described in this section, the present invention exploits the advantages of both separation methods, and minimizes their disadvantages, by coupling ITP stacking with CZE separation. In particular, the method employs conditions that allow for initial small-volume stacking by ITP, followed by a transition to CZE once ITP stacking is achieved.

Figure 6A:
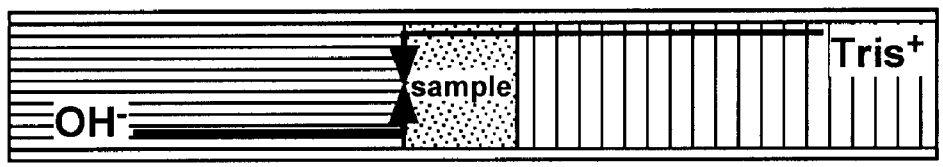
FIGS. 6A and 6B illustrate the moving reaction boundary in the ITP method of the invention.

In one general embodiment, suitable for the system illustrated in FIG. 1A, the method takes advantage of the electrolytic ions, that is, hydroxyl ions and protons, that are generated when a potential difference is placed across the two electrodes in the system. In the electrode configuration shown in FIGS. 2A and 2B, hydroxyl ions are generated at the cathode in contact with the trailing-edge electrolyte, and protons at the opposite anodic electrode, as shown in FIG. 6A. As the hydroxyl ions in the trailing-edge electrode migrate through this electrolyte, they titrate species with ionizable acid, base and hydroxyl groups, that is, groups with pH-dependent ionizable protons. The titratable species in the trailing-edge electrolyte may be the negatively charged trailing-edge species, e.g., TAPS, or the buffer counter-ion, e.g., TRIS, of the trailing-edge ion.

Figure 6B:
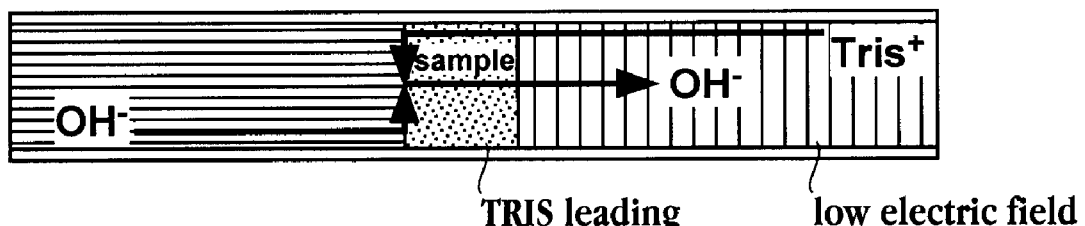

As the hydroxyl ions migrate through the trailing-edge electrolyte, they neutralize the titratable species, e.g., TRIS buffer, in the trailing-ion buffer. When the hydroxyl ions have fully migrated through the trailing-ion electrolyte, they continue migration in a downstream direction through the sample region, which may contain additional titratable species, e.g. TRIS buffer ions. When the hydroxyl ions migrate into and through the sample components, they displace the slower-moving trailing ions, effectively disrupting the interface between the slowest moving sample components and the trailing edge electrolyte. As the hydroxyl ions migrate through the sample band, as indicated in FIG. 6B, they disrupt the interface between the fastest-moving sample components and the leading-edge electrolyte. At this point, the sample components are stacked in a medium that contains hydroxyl ions as both leading and trailing ions. Under these conditions, the bands are free to migrate and separate according to normal electrophoretic separation.

More generally, for a sample containing leading-edge ions, the transition from ITP to CZE occurs when the sample ions begin to overtake trailing ions in the trailing-edge electrolyte. In samples containing trailing-edge ions, the transition occurs when the leading edge ions in the upstream channel portion begin to overtake the sample ions. With continued application of the sample-injection voltage, the prestacked components are further separated by CZE.

In accordance with the invention, the concentration of titratable species in the trailing-ion electrolyte is selected, in relation to the lengths of the upstream channel region and the sample-loading volume, to permit the sample to stack into a relatively small sample volume before electrolytic-ion, e.g., hydroxyl, migration from the upstream electrode into and through the sample-loading region is effective to overtake the charged sample components. Thus, higher concentrations of titratable species in the trailing-edge electrolyte, and larger the volume (length of the upstream channel region), the longer period of time needed for hydroxyl ion generated at the upstream electrode to overtake the sample components. In addition, since titratable ions in the leading-edge electrolyte, e.g., TRIS ions, can migrate from the LE electrolyte to the TE electrolyte, the concentration of titratable species, e.g. TRIS ions, in the LE electrolyte can also influence the rate at which hydroxyl ions migrate into and through the sample region.

In another general embodiment, suitable for the system illustrated in FIG. 1B, the method involves first applying an electric field across the channel, between an upstream reservoir containing a TE buffer and the downstream channel reservoir, then applying an electric field across another upstream reservoir containing hydroxyl or hydrogen ions (protons), and the downstream channel reservoir, to draw hydroxyl or hydrogen ions into and through TE electrolyte in the channel, as above. The electrode switching is timed so that the sample components are able to stack into a small volume before hydroxyl or hydrogen ions overtake the sample and destroy the TE/LE gradient conditions necessary for ITP stacking.

Figure 7:
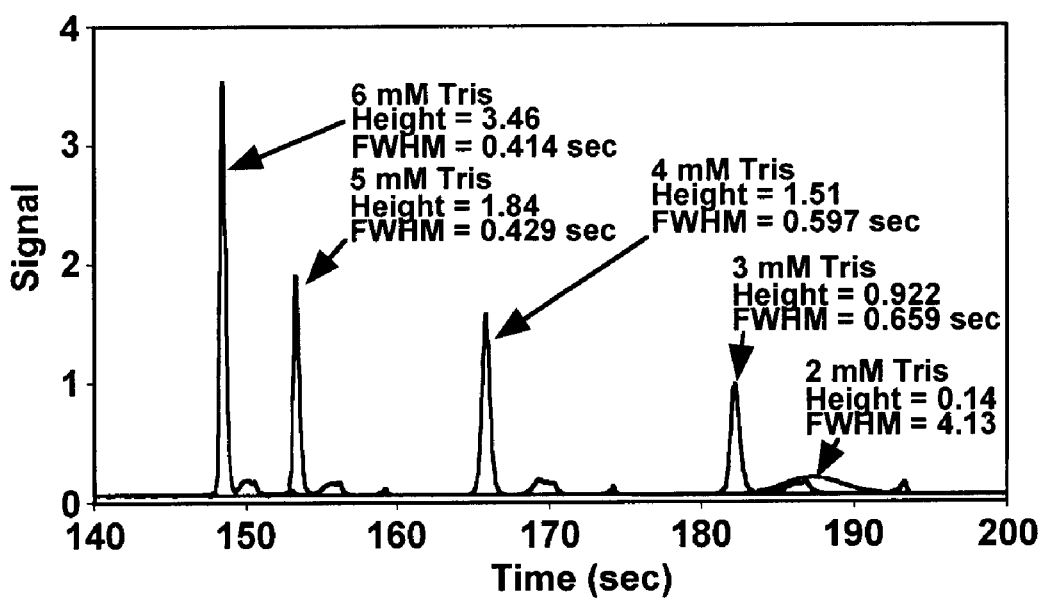
FIG. 7 shows is a plot of component resolution in the method of the invention, as a function of buffer concentration in the leading-edge buffer used.

FIG. 7 illustrates the effect of the concentration of TRIS buffer (the titratable species in the trailing edge electrolyte) on band resolution, in a combined ITP sample stacking/CZE band separation method in accordance with the invention. In this the leading edge electrolyte contained 2 mM chloride ions, 1% polyethylene oxide (PEO). The sample contained a fluorescent molecule in a sample volume length of 3000 microns (total sample volume of approximately 5 nL). The trailing edge buffer contained 2 mM TAPS, 1% PEO and selected TRIS concentrations of 2 mM, 3 mM, 4 mM, 5 mM, and 6 mM. The length of the separation region of the channel (downstream of the sample-volume region) was 5.5 cm, and the applied voltage was 200 V/cm.

The different migration times observed in FIG. 7 are due to the greater ITP stacking times associated with greater TRIS concentration in the trailing-edge electrolyte. Sample stacking by ITP, as evidence by the peak height of the electrophoretically run sample components, was also enhanced progressively with increasing TRIS concentration. Below a threshold TRIS concentration of about 2–3 mM, sample stacking by ITP was inadequate to produce an easily detected sample band.

It will be appreciated from above that successful practice of the invention involves a consideration of three variables. The first is the concentration of sample components in a given sample, and in particular, the concentration of the lowest-concentration sample component that is to be detected. The second variable is sample volume, and in particular, the sample volume needed to detect the lowest-concentration sample component. Within the constraints of a given detection method, e.g., detection of sample flourescence, a certain minimum molar amount of sample component is required, and this will determine the total volume of sample required. The third variable is concentration of titratable species in the trailing-edge electrolyte, as illustrated by the effect seen in FIG. 7. For a given sample volume, the concentration of titratable species must be high enough to allow for ITP stacking prior to the transition to CZE.

In one general embodiment of the invention, the sample volume is fixed, for example, with a single channel network of the type illustrated in FIG. 1. In this embodiment, the concentration of titratable species in the trailing-edge electrolyte will be selected to allow for good sample stacking by ITP, prior to the transition to CZE. The TRIS concentrations used in the method illustrated in FIG. 7 provide guidance for this selection. Based on a total sample volume of 5 nL, and sample-volume length of 3000 microns, a TRIS concentration of 5–6 mM would be selected. The selected TRIS concentration would be proportionately higher or lower for greater or lesser sample volumes and sample-region lengths.

The concentrations of the electrolytes will generally be in the range of about 0.1 to 1,000 mM, more usually in the range of about 1 to 50 mM. For the terminating electrolyte, the range will generally be about 1 to 50 M, while for the leading electrolyte, the range will generally be from about 1 to 1000 mM. The sample concentration may also vary widely, depending on the nature of the sample, the number of components, the ease with which they can be separated, etc. Generally, the total concentration of the components of the sample to be assayed will be in the range of about 0.1 pM to 1 $\mu$M.

Illustrative electrolytes (refers primarily to the salts that are used to provide the leading and terminating ions include, sodium chloride, HEPES, TAPS, sodium citrate, sodium phosphate, sodium borate, sodium tetraborate, sodium taurodeoxycholate, CAPS, sodium glycinate, Tris-Cl, sodium formate, sodium ethane sulfonate, sodium pentane sulfonate, sodium tartrate, etc. While Tris and sodium are the most common counter-ions, they may be replaced with ammonium, lithium, potassium, magnesium, etc., for the cations, and bromide, nitrate, nitrite, sulfate, cyanide, etc. for the anions, as well as by the electrolyte ions indicated above. The ionic strength of the sample as compared to the electrolyte solution in the main channel may vary widely, may be less than, be at least equal to or greater than the ionic strength of the electrolyte solution in the main channel. This can be achieved by the addition of salts, such as alkali metal chlorides to the sample solution, in the range of about 5 to 250 mM, more usually in the range of about 5 to 100 mM, and preferably in the range of about 20 to 75 mM.

In another general embodiment, the invention provides a plurality of different devices with different channel-volumes, e.g., different length channel-volume regions, which can be selected to provide a minimum sufficient volume for the particular sample to be analyzed. For example, the ratio of lengths of the sample-volume region to the length of the separation channel can vary from a minimum of about 1:50 to a maximum of about 1:1. As the ratio of the two lengths increases, more sample can be applied, allowing detection of lower concentration components, but requiring a greater concentration of titratable species in the TE electrolyte. Selection of the concentration of titratable species required would follow the guidance provided above.

In operation, after the sample-loading step, the control unit (FIG. 1) operates to apply a voltage potential across the upstream and downstream portions of the electrolyte channel, as illustrated in FIG. 5B, as part of the sample-injection step. Now the sample components will become stacked in accordance with their mobility as the sample ions move through the sample volume.

It will be appreciated that the roles of the leading and terminating ions can be reversed in the method just described, where leading ions are supplied from reservoir 20, terminating ions from reservoir 40, sample from reservoir 42, and leading ions from reservoir 24.

C. Exemplary Methods

The combined ITP/CE method was compared against conventional CZE for resolution and sensitivity in detecting low-concentration sample components. For CZE, the buffer was 6 mM TRIS, 2 mM Cl, 1% PEO. The initial injection volume was approximately 0.4 nL, corresponding to an initial injection plug length of 250 microns. The ITP buffer was for the LE, 6 mM TRIS, 2 mM Cl, and 1% PEO, and for the TE, 6 mM TRIS, 2 mM TAPS, and 1% PEO. The initial injection plug was 3 mm in length. The sample containing ACLA 160F and ACLA 177F, both at the same concentration, which was varied between 250 pM and 500 fM.

Figure 8A:
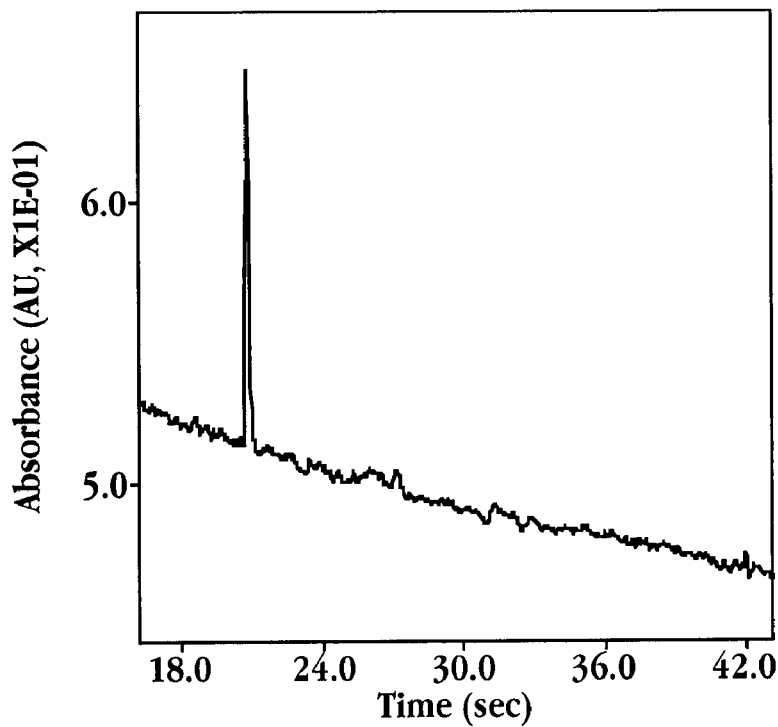
FIGS. 8A and 8B illustrate the sample-component sensitivity achievable with capillary zone electrophoresis (CZE) alone (FIG. 8A), and the combination of ITP and CZE carried out in accordance with the present invention (FIG. 8B), at 250 pM sample.
Figure 8B:
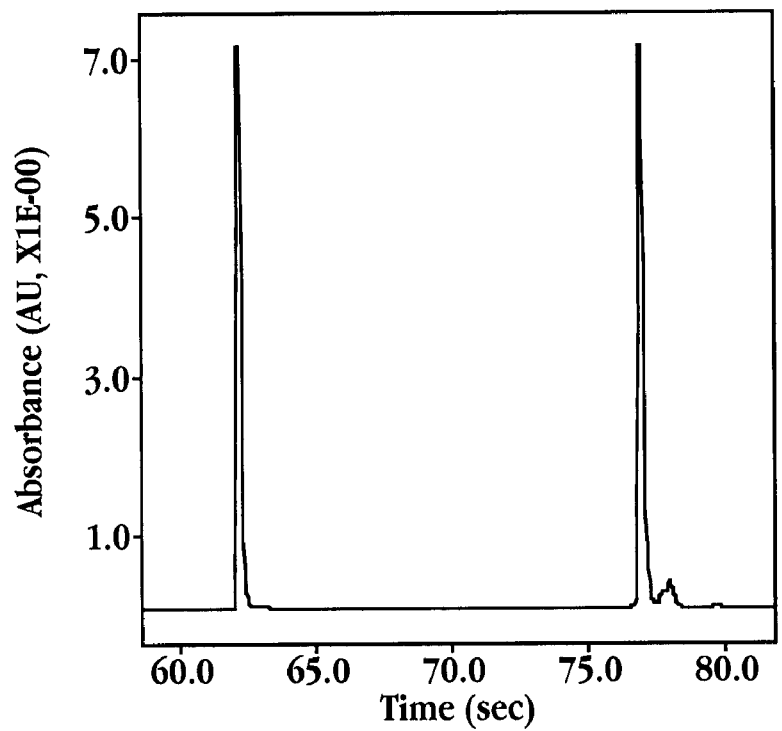

FIGS. 8A and 8B show electrophrerograms for the sample material in which each sample components was present at a concentration of 250 pM. As seen, the combined ITP/CZE method (8B) gave sharper peaks, higher resolution, and lower signal-to-noise when compared with CZE alone (8E).

Figure 9A:
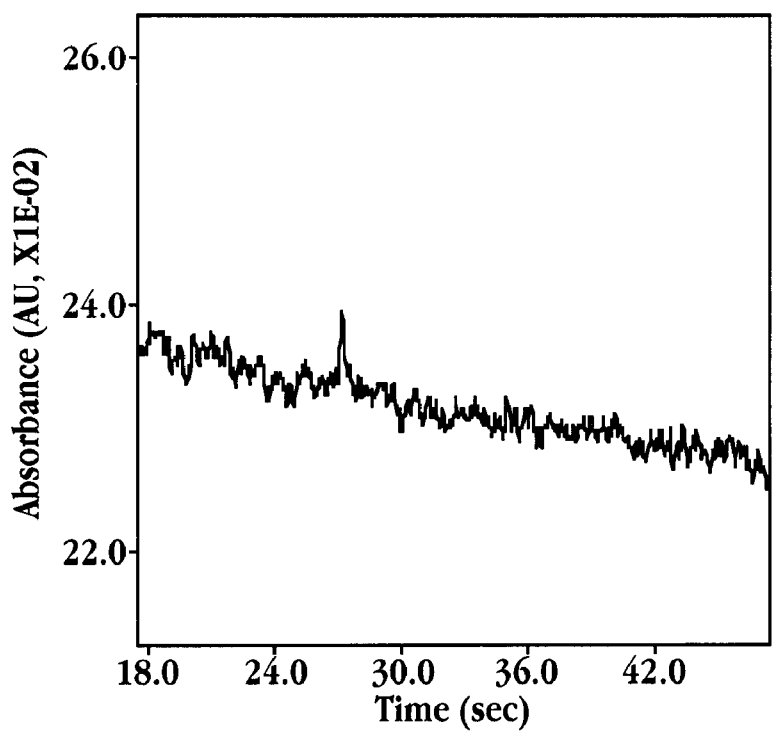
FIGS. 9A and 9B illustrate the sample-component sensitivity achievable with capillary zone electrophoresis (CZE) alone (FIG. 9A), and the combination of ITP and CZE carried out in accordance with the present invention (FIG. 9B), at 50 pM sample.
Figure 9B:
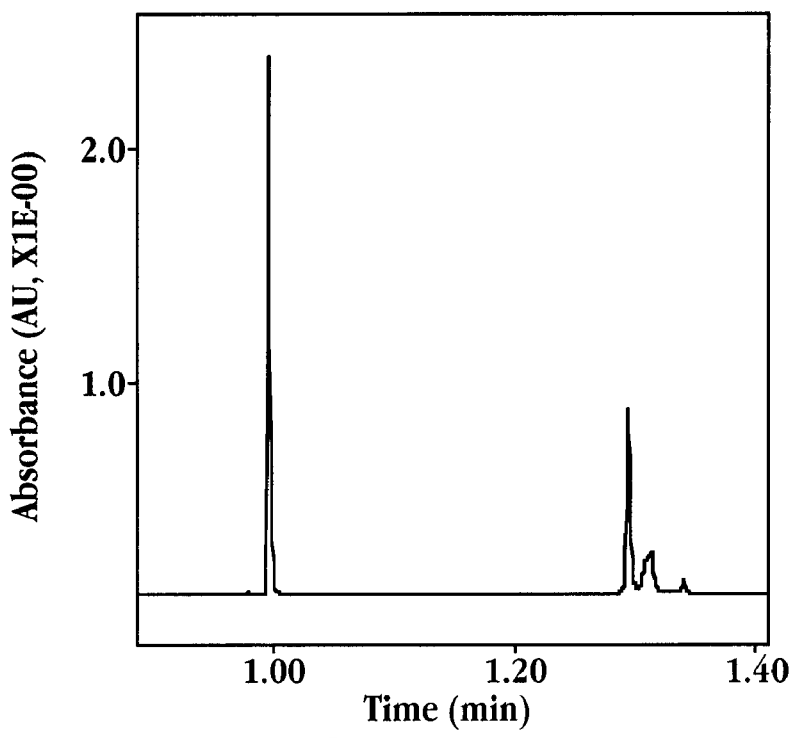
Figure 10A:
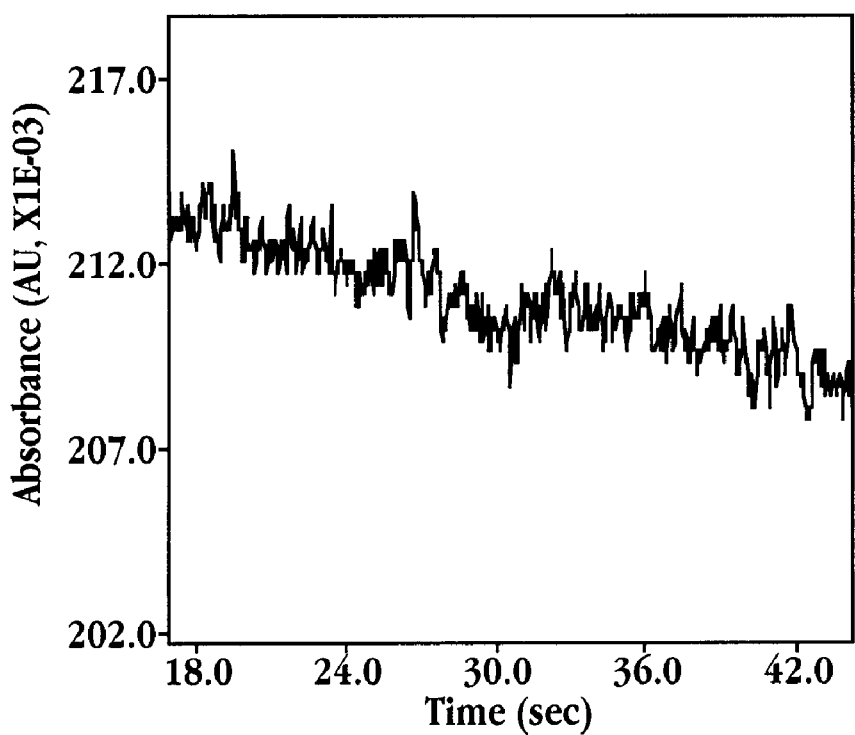
FIGS. 10A and 10B illustrate the sample-component sensitivity achievable with capillary zone electrophoresis (CZE) alone (FIG. 10A), and the combination of ITP and CZE carried out in accordance with the present invention (FIG. 120), at 5 pM sample.
Figure 10B:
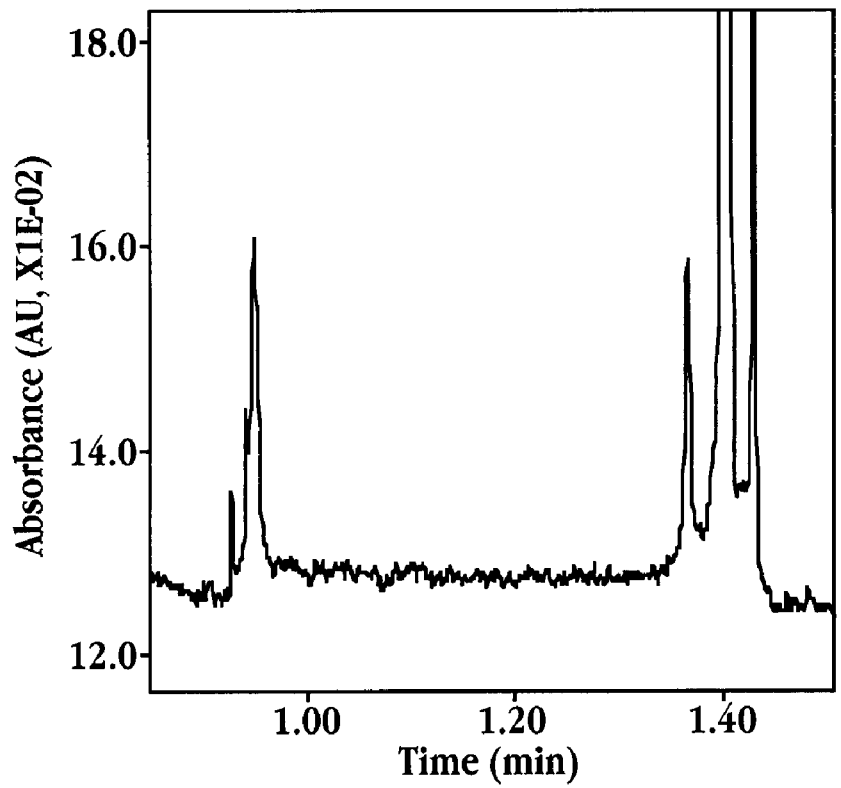
Figure 11A:
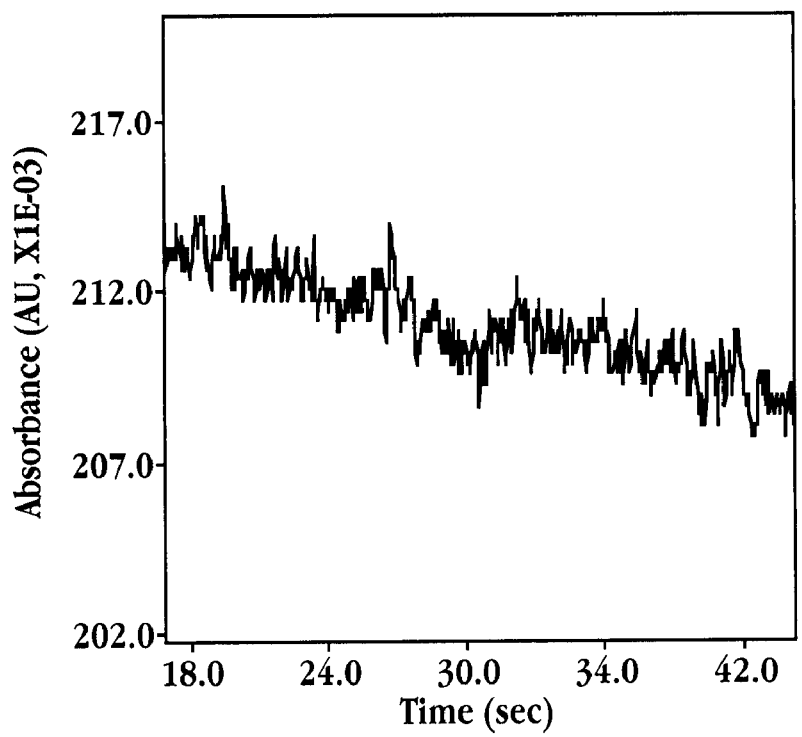
FIGS. 11A and 11B illustrate the sample-component sensitivity achievable with capillary zone electrophoresis (CZE) alone (FIG. 11A), and the combination of ITP and CZE carried out in accordance with the present invention (FIG. 11B), at 500 fM sample.
Figure 11B:
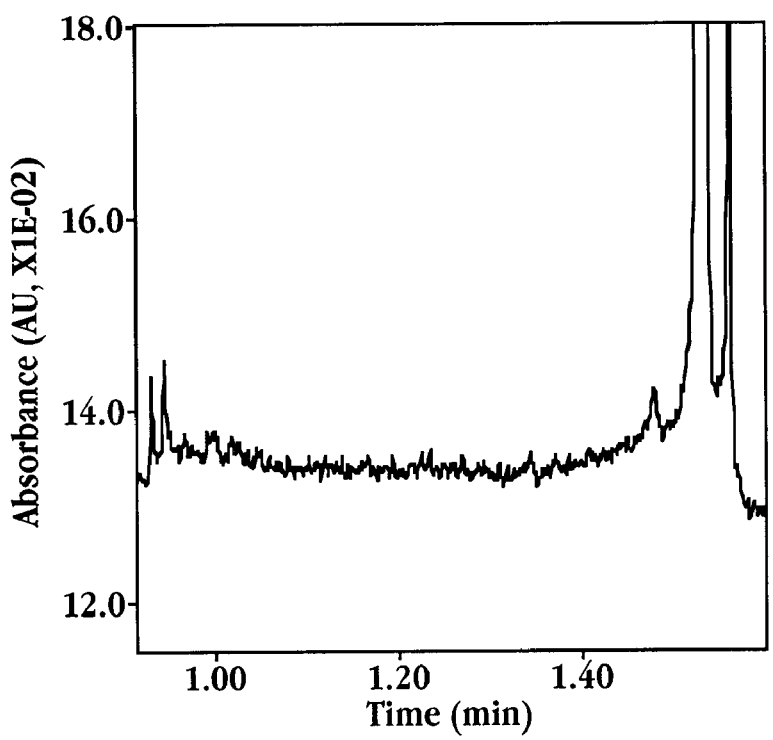

The advantages of the combined methods become more striking at lower sample concentrations, as seen in FIGS. 9A and 9B for sample concentrations of 50 pM, Figs. for sample concentrations of 5 pM, and FIGS. 11A and 11B for sample concentrations of 500 fM.

More generally, the present method provides an improved sample separation method that allows high resolution, sharp peaks and high signal-to-noise ratios for samples, particularly for samples that are too dilute to resolve by ITP and too dilute to detect by CZE.

VI. Combined Sample Treatment and Separation

One application of the present method is in separation electrophoretic tags contained in a sample of tags, typically at dilute tag concentrations. Such tags are typically generated by target-specific cleavage of electrophoretic probes, when the probes are bound to a probe-specific target. Electrophoretic probes and tags of this type, and methods for their use in multiplexed assays are described, for example in co-owned PCT patent application PCT/US00/11396 which is incorporated by reference herein.

In one multiplex-probe embodiment, each probe is composed of a target-specific moiety designed to bind to a sample target and a multi-tag reporter attached to the target-specific moiety through a target-specific cleavage site at which the reporter can be cleaved from the moiety by a target-specific cleaving agent. Each reporter, in turn, includes a backbone structure, such as a branched polymer, and a plurality of electrophoretic tags attached to the structure through cleavable linkages, Preferably the linkages are photolytic, although chemical-cleavage linkages, such as disulfide or enzyme-cleavable linkages, are also contemplated. A portion of the channel network contains a sample-loading region. The sample material placed in the sample-loading region in this example is a probe mixture that results from reacting a plurality of different target-specific probes, and cleaving those probes that react with, e.g., bind to targets. Thus, the sample mixture includes uncleaved probes and cleaved reporters. The probes and cleaved reporters have opposite net charges at the pH of the ITP buffer used in the method, so that the two migrate in opposite directions when subject to an electric field during the initial ITP stage of separation.

After sample stacking, but before the transition from ITP to CZE, the cleaved reporters are exposed to lytic conditions effective to release electrophoretic tags from the reporters. The lytic condition may be selective irradiation through a photomask to photolytically release the tags from the reporters, or localized chemical conditions, e.g., photo-activation of an agent in the ITP buffer capable to producing singlet oxygen under irradiation conditions. The critical feature is localized tag release, so that tags associated with cleaved reporters are released, but tags associated with uncleaved probe is not. As noted above, the released tags represent one or more detectable electrophoretic tags with different electrophoretic mobilities for each different released reporter.

After the transition from ITP to CZE, the different released tags will separate electrophoretically, producing resolved electrophoretic tags with known electrophoretic mobilities. Where the tags have visibly detectable groups, e.g., fluorescent groups, the bands can be directly detected. From the known mobilities of each tag, the probes from which the tags were released can be determined, as well as the presence of the associated probe target in the sample. Alternatively, the tags may have catalytic groups effective to catalyze a detectable color reaction, in the presence of selected reagents. In this embodiment, the tags may be mixed combined successively with the detection reagent in a system.

The invention now having been fully described, it will be apparent to one of ordinary skill in the art that many changes and modifications can be made thereto without departing from the spirit or scope of the appended claims.

What is claimed is:

1. A method of separating components having a given negative or positive charge and contained in a sample, comprising
   (a) loading a separation microchannel having, in an upstream to downstream direction, an upstream end, an upstream channel region, a sample-volume channel region, a downstream separation channel region, and a downstream end, so as to fill
      (i) the upstream channel region with a trailing-edge electrolyte containing a trailing edge ion having an electrophoretic mobility lower than that of any of the sample components, and containing a selected concentration of a titratable species,
      (ii) the sample-volume channel region with the dilute sample, and
      (iii) the separation channel region with a leading-edge electrolyte, containing a leading edge ion having an electrophoretic mobility greater than that of any of the sample components; and
   (b) creating an electrical field potential across said microchannel, by applying a voltage potential across electrodes in contact with said upstream and downstream channel ends,
   thereby causing charged components in said sample to stack by isotachophoresis, and subsequently causing hydroxyl or hydrogen ions to migrate into the trailing-edge electrolyte, titrating said titratable species therein, under conditions that permit the sample to stack into a relatively small sample volume before hydroxyl- or hydrogen-ion migration into and through the sample-volume region is effective to overtake the charged sample components,
   wherein continued application of an electric potential across the channel ends causes charged sample components in the stacked sample volume to separate by zone electrophoresis.

2. The method of claim 1, wherein said upstream channel region includes a pair of upstream reservoirs, one containing the trailing-edge electrolyte, and the other containing a source of said hydroxyl or hydrogen ions, and said creating includes initially applying a voltage potential across electrodes in contact with said one upstream reservoir and the downstream channel end, and subsequently, applying a voltage potential across electrodes in contact with said other upstream reservoir and the downstream channel end.

3. The method of claim 1, wherein the upstream channel region is filled with a trailing-edge electrolyte containing a selected concentration of a titratable species, and said applying is effective to cause charged components in said sample to stack by isotachophoresis, and, at the same time, to cause electrolytic hydroxyl or hydrogen ions, formed by electrolysis at the upstream-end electrode, to migrate into the trailing-edge electrolyte, titrating said titratable species therein,
   where the concentration of said titratable species in the trailing-edge electrolyte is selected, in relation to the lengths of the upstream channel region and sample-loading volume, to permit the sample to stack into a relatively small sample volume before electrolytic-ion migration from the upstream electrode into and through the sample-volume region is effective to overtake the charged sample components, and wherein continued application of an electric potential across the channel ends causes charged sample components in the stacked sample volume to separate by zone electrophoresis.

4. The method of claim 3, wherein the trailing-edge electrolyte includes a trailing-edge ion and a titratable counter-ion buffer at said selected concentration.

5. The method of claim 4, wherein the electrolytic ions formed at the upstream-end electrode are hydroxyl ions, and the titratable counter-ion buffer is a TRIS buffer.

6. The method of claim 1, for use in detecting charged sample components present at nanomolar concentrations or less, wherein the ratio of sample volume before and after isotachophoretic stacking is at least about 10:1.

7. The method of claim 6, wherein the ratio of sample volume before and after isotachophoretic stacking is at least about 50:1.

8. The method of claim 7, for use in detecting charged sample components present at picomolar or less concentrations, wherein the ratio of sample volume before and after isotachophoretic stacking is at least about 100:1.

9. The method of claim 1, wherein the ratio of the lengths of the sample-volume region to the separation channel is between about 1:50 to 1:1.

10. The method of claim 1, wherein said ratio is between about 1:10 to 1:2.

11. The method of claim 3, wherein the leading-edge electrolyte contains a negatively charged leading-edge ion having an effective conductivity greater than that of the sample ions and a concentration between 1–50 mM, the trailing-edge electrolyte contains a negatively charged trailing-edge ion having an effective conductivity lower than that of the sample ions and a concentration of between 1–50 mM, and both electrolytes have a positively charged buffer at a selected concentration between about 2 and 50 mM.

12. The method of claim 1, wherein the separation microchannel is part of a channel network in a microfluidics device, which also includes first and second side channels which intersect the separation channel at axially spaced intersections, defining said sample-volume region between said intersections, and said loading includes moving said sample from a sample reservoir connected to the first side channel through the sample-volume region and into the second side channel.

13. The method of claim 1, for use in separating a plurality of electrophoretic tags contained in a sample, each tag having a detectable moiety and a mobility modifier that confers on the tag, a unique electrophoretic mobility, which further includes the steps, after separating the tags electrophoretically, of detecting the separated tags, and determining from their electrophoretic mobilities, the identify of probe from which the tags were cleaved.

14. The method of claim 13, wherein said tags are contained on branched polymer structures and linked thereto through photo-labile linkages, and said method further includes, after permitting branched structures in the sample to stack into a relatively small sample volume, irradiating the branched structures to release the tags therefrom, wherein continued application of an electric potential across the channel ends causes said tags in the stacked sample volume to separate by zone electrophoresis.

* * * * *